United States Patent [19]

Kramer

[11] 4,310,249
[45] Jan. 12, 1982

[54] SPECTROPHOTOMETER

[75] Inventor: Donald L. Kramer, Elkhart, Ind.

[73] Assignee: Miles Laboratories, Inc., Elkhart, Ind.

[21] Appl. No.: 82,674

[22] Filed: Oct. 9, 1979

[51] Int. Cl.³ .............................................. G01J 3/50
[52] U.S. Cl. .................................. 356/414; 356/432; 356/236; 250/228
[58] Field of Search ............... 356/414, 236, 73, 432, 356/436, 440; 250/228

[56] References Cited
U.S. PATENT DOCUMENTS

| | | | |
|---|---|---|---|
| 3,432,243 | 3/1969 | Hardesty | 356/236 X |
| 4,076,421 | 2/1978 | Kishner | 356/236 X |
| 4,120,582 | 10/1978 | De Vries et al. | 356/236 X |
| 4,171,909 | 10/1979 | Kramer et al. | 356/73 |

FOREIGN PATENT DOCUMENTS 2757196  6/1979  Fed. Rep. of Germany ...... 356/432

Primary Examiner—F. L. Evans
Attorney, Agent, or Firm—Roger N. Coe

[57] ABSTRACT

Apparatus for measuring transmitted light is described. The apparatus comprises a spectrophotometer which includes a light source; first and second diffusion chambers; a cuvette chamber and photodetection means.

The apparatus also includes light transmitting channels through which light can pass from said source to the first diffusion chamber, from the first diffusion chamber through the cuvette chamber to the second diffusion chamber, and from the second diffusion chamber to the photodetector means.

In the preferred embodiment the first and second diffusion chambers are light diffusing integrating spheres, and a filter is present in the light transmission channel between the light source and first diffusion chamber.

3 Claims, 2 Drawing Figures

SPECTROPHOTOMETER

FIELD OF THE INVENTION

The present invention relates to transmission type spectrophotometers and, more particularly, the present invention relates to transmission type spectrophotometers which are capable of achieving reproducible results using conventional cylindrical cuvettes.

BACKGROUND OF THE INVENTION

Transmittance type spectrophotometric measurements are normally made by simply directing a light through a cuvette containing a fluid sample to be analyzed. A portion of the light beam is absorbed by the sample and the remaining portion passes through the cuvette to photodetector means for measurement. By comparing the measurement obtained from the sample with a measurement obtained from a control fluid the concentration of the analyzed sample can be calculated.

A major source of error in spectrophotometer systems lies in imperfections in the glass or plastic cuvette walls. These imperfections alter the nature of the light beam which passes to the photodetector means and very minor variations in a cuvette will substantially affect measurements made by the photodetector means. Distortion of the light beam passing through a cuvette means that it is impossible to obtain reproducible results. This is particularly true for spectrophotometers in which a slit or window is located adjacent to the photodetector means for the purpose of selectively regulating measurements which are made.

In order to compensate for the aforementioned problem highly accurate spectrophotometer systems utilize optically ground and polished glass or quartz to form cuvettes for holding specimens to be analyzed. These cuvettes have at least two sides which are parallel surfaces of extremely high uniformity, thereby effectively minimizing all distortion of light passing through the cuvettes. Needless to say, such cuvettes are very expensive to manufacture. For this reason accuracy is normally sacrificed by using conventional cylindrical cuvettes resembling test tubes in transmission type spectrophotometers.

SUMMARY OF THE INVENTION

An object of the present invention is to provide an improved spectrophotometer.

Another object of the present invention is to provide an accurate spectrophotometer capable of making reproducible transmittance measurements.

Still another object of the present invention is to provide a spectrophotometer that utilizes standard cuvettes and which is not adversely affected by the rotational orientation of a cuvette in the spectrophotometer.

In accordance with the present invention, a fluid sample in a conventional cylindrical cuvette is illuminated by diffused light reflected from the walls of a diffusion chamber. After the diffused light passes through the sample it enters another diffusion chamber before being measured by photodetector means. Refractions caused by imperfections in the sample-containing cuvette are integrated by the diffusion chambers and the resulting distortion becomes negligible when the final measurement is made by the photodetector means.

BRIEF DESCRIPTION OF THE DRAWINGS

Other and further objects, advantages and features of the invention will be apparent to those skilled in the art from the following detailed description thereof, taken in conjunction with the accompanying drawings in which.

DESCRIPTION OF THE PREFERRED EMBODIMENTS

Figure 1:
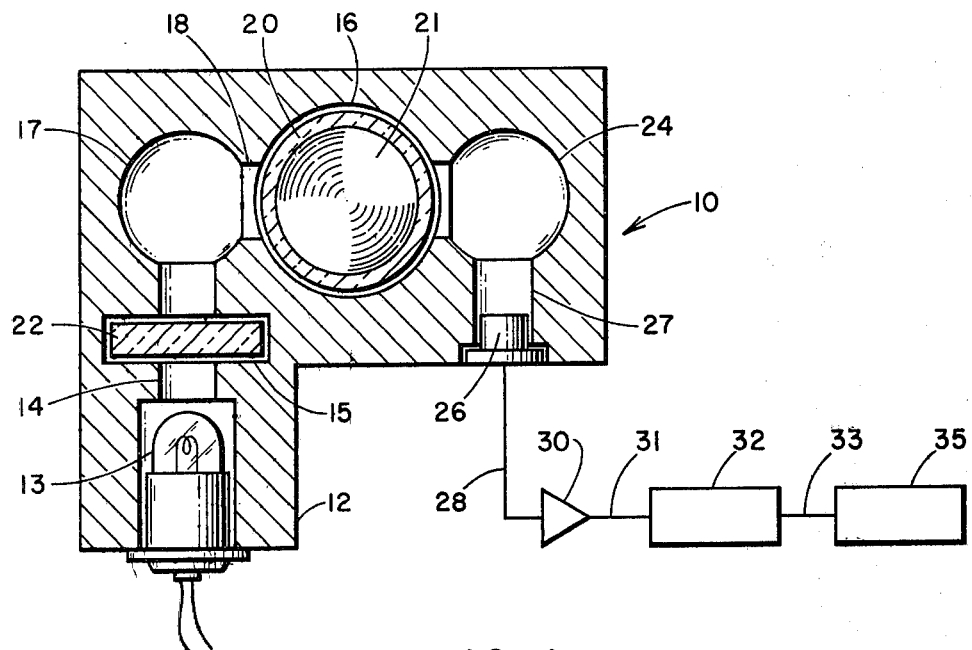
FIG. 1 is a diagrammatic top view, in partial cross section, illustrating a spectrophotometer in accordance with the present invention.

Referring now to the drawings, a spectrophotometer in accordance with the present invention is illustrated in FIG. 1. Spectrophotometer 10 comprises a housing 12 formed with a bore 14 having a light source mounted in its outer end, the latter being connected to a suitable power source (not shown). At its inner end bore 14 radially intersects a spherical diffusion chamber 17. Housing 12 is also formed with a bore 18, one end of which radially intersects chamber 17 with its axis normal to the axis of bore 14 and coplanar therewith. The other end of bore 18 radially intersects a spherical diffusion chamber 24 which is similar to the chamber 17. A bore 27 has photodetector means 26 mounted in its outer end, and the inner end thereof radially intersects diffusion chamber 24 with its axis normal to that of bore 18 and coplanar therewith. Housing 12 is also formed with a transverse bore or recess 16 which diametrically intersects bore 18 and is sized to removably accommodate a test tube-shaped cuvette 20 containing a liquid sample 21.

Bores 14, 18 and 27 provide cylindrical channels through which light can pass from light source 13 to diffusion chamber 17, from diffusion chamber 17 through cuvette 20 to diffusion chamber 24, and from diffusion chamber 24 to photodetector means 26. If desired, the housing 12 may also be formed with a recess 15 which intersects bore 14 and accommodates a suitable filter 22 which permits only light of a specific wavelength to pass through bore 14 from source 13 to diffusion chamber 17.

Photodetector means 26 is connected via line 28 to a signal amplifier 30, which, in turn, is connected by line 31 to an analog/digital converter 32. Converter 32 is connected by line 33 to display means 35 for digital display and/or recordation of light sensed by the photodetector means 26.

Thus, light from light source 13 passes through a light transmission path to diffusion chamber 17 and diffused light from diffusion chamber 17 is transmitted via a light transmission path through cuvette 20 and sample 21 therein into diffusion chamber 24; and diffused light from diffusion chamber 24 passes through still another light transmission path to photodetection means 26. The measurement made by photodetection means 26 is ultimately displayed or recorded by display means 35.

Housing 12 can be made of any suitable material. For example, it can be machined from metal or it can be molded from plastic.

The light source 13 can be any suitable light source which in conjunction with filter 22 provides a suitable reading at photodetector means 26 for the particular sample 21 which is analyzed. Preferred light sources are light sources which produce a white light having spectral characteristics typical of a black body operating at 20,000° Kelvin and which produce a light characteristic of at least 5,000° Kelvin. The duration of such a light source is preferably between one microsecond and about 100 microseconds although it will be understood that the duration can for special applications be either shorter or longer. Particularly advantageous is the use of a rapidly pulsed flash tube, such as a xenon flash tube. Such a flash tube allows construction of a very compact versatile spectrophotometer. It will be understood that the axis of light channel bore 14 can be positioned at an angle other than 90° with respect to the axis of light channel bore 18 which connects diffusion chamber 17 with diffusion chamber 24. However, the axis of bore 14 should not be in direct alignment with that of bore 18.

Depending on the light source utilized and the measurement to be made, filter 22 can be omitted. Normally, however, a filter, such as an interference filter, is used. Typically, such filters permit the transmission of light having a wavelength from about 250 nanometers (nm) to about 800 nm. If desired, filter 22 can be formed into a cartridge format (not shown) to permit the ready insertion or withdrawal of such filter from recess 15 depending on the sample being analyzed. Another embodiment which can be used comprises a wheel (not shown) having multiple filters, said wheel being suitably mounted for rotation in the housing 12 so that upon rotation, a selected filter can be positioned in recess 15.

Preferably, bore or light channels 14, 18 and 27 are painted or coated dull black to minimize reflection of light passing therethrough. The interiors of diffusion chambers 17 and 24, on the other hand, are preferably white. The interior surfaces of these integrating type spheres should be highly reflective. It has been found that an integrating sphere coated on the interior with magnesium oxide, barium sulfate, HALON resin (polytetrafluoroethylene) made by Allied Chemical Corporation of Morristown, N.J., or the like, provides a satisfactory reflective surface. The size of the diffusion chambers 17 and 24 is not critical and the chambers need not be identical in size or interior finish. Diffusion chambers as small as ping pong balls can be used successfully.

It will be understood that while light source 13 and photodetection means 26 have been illustrated as lying on the same side of housing 12, they could be positioned on opposite sides of said housing. Light channel bores, 14, 18 and 27 should be adequate in size and of such configuration to transmit essentially collimated light from light source 13 to diffusion chamber 17 and from diffusion chamber 24 to photodetection means 26, respectively. If desired, spaced inwardly directed annular flanges or light baffles (not shown) defining coaxial openings can be employed in bores 14, 18 and 27 to aid in collimating light passing therethrough.

The recess 16 should be just large enough to accommodate a standard cylindrical cuvette, i.e., test tube. Cuvette 20 can be made of glass or plastic or any other suitable transparent material which will permit the transmission of diffused light from diffusion chamber 17 through fluid sample 21 into diffusion chamber 24.

Any suitable sensor can be used as photodetection means 26. For example, solid state silicone photodiodes, such as Model UV 100B made by E. G. & G. Inc. of Salem, Massachusetts and Model S876-33BQ made by Hemamatsu Corp., Middlesex, N.J., can be employed. Photodetector 26 can be fitted tightly into bore 27 in such a manner as to minimize the effect of extraneous light sources, such as ambient light conditions.

Amplifier 30, analog/digital converter 32 and display means 35 are all conventional, well known hardware. If desired these items could be incorporated into housing 12.

Figure 2:
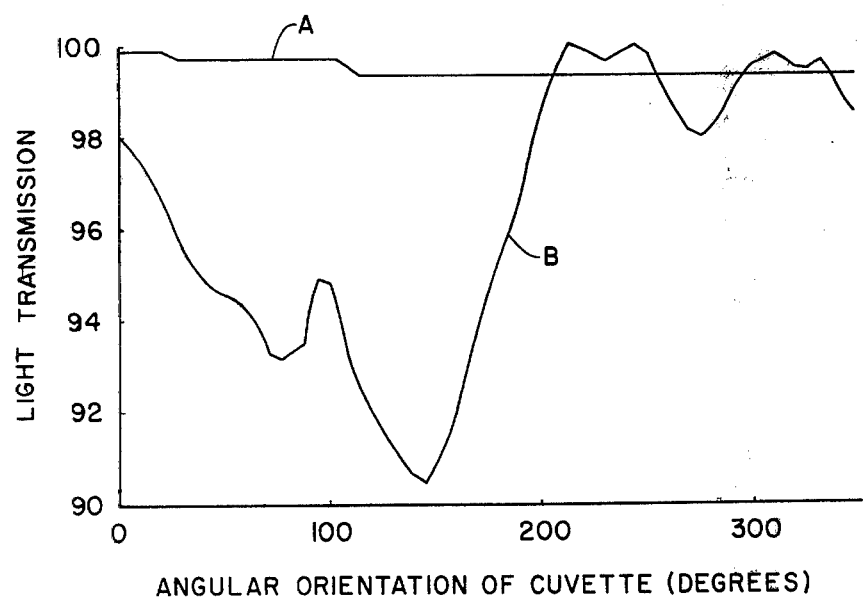
FIG. 2 is a graph illustrating the change in the transmission of light through a water-filled conventional cylindrical cuvette as the cuvette is axially rotated 360° in its holder using (A) the spectrophotometer of FIG. 1 and (B) a normal transmission type spectrophotometer.

FIG. 2 compares changes in transmission of light through a water filled cuvette as the cuvette is axially rotated through 360°. These changes are caused by imperfections in the cuvette walls primarily due to the lack of uniformity in side wall thickness, the lack of side wall homogeneity and the absence of parallelism between side walls. Line A in FIG. 2 shows that when the system of the present invention (as illustrated in FIG. 1) is utilized there is substantially no variation in light transmission as cuvette 20 is axially rotated through 360°.

In contrast, line B shows that when a standard spectrophotometer is employed which passes light directly through the identical cylindrical test tube cuvette 20 to a photodetector, substantial variation in light transmission results as the cuvette is axially rotated through 360°. FIG. 2 thus graphically illustrates that without diffusion chambers 17 and 24, as illustrated in FIG. 1, it is impossible to obtain reproducible results using conventional cuvettes.

From the foregoing, it will be seen that this invention is well adapted to attain all of the ends and objects hereinbefore set forth, together with other advantages which are obvious and inherent. The improved spectrophotometer of the present invention permits high accuracy to be obtained by relatively unskilled personnel with inexpensive cuvettes. As indicated, the rotational orientation of the cuvette 20 does not substantially affect light transmission in the improved spectrophotometer herein described. This is significant in that it means that reproducible results are now possible using inexpensive conventional cylindrical cuvettes or test tubes.

Obviously, many modifications and variations of the invention as hereinbefore set forth can be made without departing from the spirit and scope thereof and therefore only such limitations should be imposed as are indicated by the appended claims.

What is claimed is:

1. Spectrophotometer apparatus comprising:
    a discontinuous light source capable of producing a light characteristic of at least 5,000° K for a duration of from about one microsecond to about 100 microseconds;
    a first light integrating sphere capable of uniformly diffusing light from said light source;
    means defining a first light transmission path for the passage of light from said light source to said first light integrating sphere;
    a second light integrating sphere capable of uniformly diffusing light;
    a cylindrical liquid sample cuvette positioned between said first and second light integrating spheres;
    means defining a second light transmission path for the passage of light from said first light integrating sphere through said sample cuvette to said second light integrating sphere, said second light transmission path being aligned at an angle to the first light transmission path;
    photodetection means; and
    means defining a third light transmission path for the passage of diffused light directly from said second light integrating sphere to said photodetection means, said third light transmission path being aligned at an angle to the second light transmission path.

2. Spectrophotometer of claim 1 which also includes a filter positioned in said first light transmission path, said filter permitting the transmission of light having a wavelength of between about 250 and about 800 nanometers.

3. Spectrophotometer apparatus of claim 1 in which the third light transmission path is aligned at a right angle to the second light transmission path.

* * * * *